United States Patent [19]

Woo et al.

[11] Patent Number: 5,093,297

[45] Date of Patent: Mar. 3, 1992

[54] POLYSTYRENE IMMOBILIZED RHODIUM COMPLEX CATALYST FOR THE HYDROFORMYLATION OF OLEFINS

[75] Inventors: Seong-Ihl Woo; Ki-Su Ro, both of Seoul, Rep. of Korea

[73] Assignee: Korea Advanced Institute of Science and Technology, Seoul, Rep. of Korea

[21] Appl. No.: 587,003

[22] Filed: Sep. 24, 1990

[30] Foreign Application Priority Data

Sep. 25, 1989 [KR] Rep. of Korea ............... 1989-13783

[51] Int. Cl.$^5$ .............................................. B01J 31/28
[52] U.S. Cl. .................................. 502/155; 502/152; 502/159; 502/161; 502/167
[58] Field of Search ............... 502/155, 152, 159, 161, 502/167

[56] References Cited

U.S. PATENT DOCUMENTS 4,323,698 4/1982 Haag et al. ..................... 502/159

OTHER PUBLICATIONS

Grubbs et al., J. Am. Chem. Soc. 93, 3062–3063, (1971).
Pittman, C. U., Smith, L. R., Hanes, R. M., Journal Of The American Chemical Society /97:7/ Apr. 2, 1975 entitled "Catalytic Reactions Using Polymer-Bound vs. Homogeneous Complexes of Nickel, Rhodium and Ruthenium", pp. 1742–1748.
Batchelder, R. F., Gates, B. C., Kuijpers, F. P. J., 6th International Congress On Catalysis, (1976), pp. 499–508 entitled "Multifunctional Catalysis by Matrix--bound Rhodium (I) Complex and Amine Groups: Application to the Aldox Process".
De Munck, N. A., Verbruggen, M. W., Scholten, J. J. F., Journal Of Molecular Catalysis, 10 (1981), pp. 313–330 entitled "Gas Phase Hydroformylation of Propylene With Porous Resin Anchored Rhodium Complexes Part I. Methods of Catalyst Preparation and Characterization".

Primary Examiner—Patrick P. Garvin
Assistant Examiner—Brent M. Peebles
Attorney, Agent, or Firm—Brooks & Kushman

[57] ABSTRACT

Olefins are hydroformylated to aldehyde in the presence of polymer immobilized rhodium catalysts. These catalysts are suit for the hydroformylation of olefins in the organic solvent or in the aqueous phase.

7 Claims, No Drawings

POLYSTYRENE IMMOBILIZED RHODIUM COMPLEX CATALYST FOR THE HYDROFORMYLATION OF OLEFINS

BACKGROUND OF THE INVENTION

1. Field of the invention

The present invention relates to a process for the preparation of polystyrene immobilized rhodium catalysts for the hydroformylation of olefins, and more particularly relates to such hydroformylation of olefins in the presence of a sulfonated polystyrene containing rhodium complexes.

2. Description of the Prior Art

Catalysts for the hydroformylation of olefins are well known in the art to produce aldehydes by hydroformylation. The reaction usually carried out by reacting an olefin with carbon monoxide and hydrogen in an organic liquid medium which contains, as catalyst, a compound based on a metal of Group VIII of the periodic classification or table of elements, and especially which contains a soluble complex formed from one of the above metal compounds and at least one organic ligand which has, in its molecule, and atom of an element of Group VA of the periodic classification, such as tertiary arsines, tertiary stibines or tertiary phosphines.

Among the catalyst systems to date envisaged, those complexes resulting from the reaction of an inorganic or organic derivative of rhodium appear the most attractive. However, a notable disadvantage of those liquid phase hydroformylation processes above described require a difficult supplementary treatment for the purpose of separating the hydroformylation products from the catalyst solution. Then, many methods have been developed for attaching transition metal complexes to a polymer support to eliminate the disadvantage of soluble catalysts.

It is well known in the prior art to use crosslinked poly(styrene-divinylbenzene) copolymer as a support for the production of a polymer immobilized catalyst. Polymer immobilized catalysts have advantages of homogeneous catalyst and heterogeneous catalyst.

It has been long recognized that the homogeneous processes suffer from the difficulties of separating the catalyst from the products and it is for this reason that methods for immobilizing transition metal species on the solid supports have been studied in detail.

Polymer immobilized catalyst has an advantage of easy recovery and possible reuse and these advantages offer to reduce the production cost.

It is well known in the prior art to make these catalysts by attaching metal catalyst on the polymer support via covalent bonding or ionic bonding. Especially, in the case of polystyrene immobilized catalyst, the catalyst has been made by attaching a metal catalyst on the crosslinked polystyrene support. This polystyrene support has been functionalized by chloromethylation and phosphination reaction. This method is well knowen prior art.

For example, Pittman et al. [J. Amer. Chem. Soc., vol. 97 (1975), page 1742-1748], hereby incorporated by reference, made a polystyrene support by chloromethylation and phosphination and attached nickel, rhodium or ruthenium complex to this support. However, these catalyst have a less catalytic activity than their homogeneous counterparts in the hydroformylation of 1-pentene.

Batchelder et al. [6th International Congress on Catalysis, (1976) page 499-508], hereby incorporated by reference, made a polystyrene support containing amine functional groups and phosphine functional groups to investigate the catalytic activity in the hydroformylation of propylene at 80° C. and 86 atm. This catalyst had a higher catalytic activity at first, however the activity decreased rapidly with reaction progress.

De Munck et al. [J. Mol. Catal., vol. 10 (1981) page 313-330], hereby incorporated by reference, made a polystyrene support by chloromethylation and chlorophosphonation and attached rhodium complex to this support containing phosphine and phosphite functional groups. However, the activity of this catalyst decreased rapidly with reaction progress in spite of milder reaction condition.

Other many report has been suggested that the metal catalyst immobilized on the polymer support has a lower activity and the activity decreased rapidly with repeated use due to the severe metal leaching.

The activity of conventional polymer immobilized metal catalyst is decreased rapidly with reaction progress and the efficiency of that catalyst has a problem due to the severe metal leaching, then these catalysts cannot be used be used commercially.

Therefore, the object of this invention is the preparation of new polystyrene immobilized rhodium catalyst which has a high activity and stability in the hydroformylation of olefins.

A further object of this invention is the preparation of new polystyrene immobilized rhodium catalyst which has a high activity in the hydroformylation of olefins in aqueous phase reaction.

SUMMARY OF THE INVENTION

This invention relates to a process for preparing polymer immobilized catalysts which are valuable as catalysts for the hydroformylation of olefins.

A further object of this invention is the preparation of the rhodium complex catalysts covalently bonded to the crosslinked polystyrene resin which are highly active and stable catalyst for the hydroformylation of olefins.

This invention relates to the modification of conventional polystyrene bearing phosphine functional groups. The high active and stable catalyst for the hydroformylation reaction can be achieved by immobilizing rhodium complexes on the polystyrene support bearing sulfonated phosphine functional groups.

DESCRIPTION OF THE INVENTION

The above objects have been achieved by the present invention.

The subject of the invention is a preparation of polystyrene immobilized rhodium catalyst for the hydroformylation of olefins. More specifically, this invention relates to the polystyrene immobilized rhodium catalyst for the hydroformylation of monoethylenically unsaturated compounds having from 2 to 20 carbon atoms, comprising linear or branched chain olefins having a terminal or internal double bond. By way of non-limiting examples, they are mentioned the ethylenic hydrocarbons such as ethylene, propylene, 1-butene, 2-methyl-1-butene, 2-butene, 1-pentene, 2-pentene, 1-hexene, 3-ethyl-1-hexene, 2-propyl-1-hexene, 2-hexene, 1-heptene, 1-octene, 3-octene, 4,4-dimethyl-1-nonene, 1-decene, 2-decene, 6-propyl-1-decene, 3-undecene, 1-dodecene, 5-tetradecene, 1-octadecene and 2-octadecene.

The hydroformylation catalyst according to the present invention is most suitably applied to the linear aliphatic monoethylenic compounds containing from 2 to 8 carbon atoms, such as ethylene, propylene, 1-butene, 1-pentene, 1-hexene, 2-hexene, 1-heptene and 1-octene.

We have found that a catalyst which has attached a similar functional group on the polymer support and an immobilized rhodium complex on this support has a high activity and stability in the hydroformylation of olefins and suit for the aqueous phase reaction.

This catalyst is made by the following procedures. Crosslinked poly(styrene-divinylbenzene) copolymer is chloromethylated and phosphinated by the conventional method [Pepper et al., J. Chem. Soc., (1953) page 4097–4105], subsequently. The sulfonation of this phosphinated polystyrene is preferably carried out at temperatures of from 15° to 130° C., especially from 60° to 120° C. with concentrated sulfuric acid. The reaction time may vary from 1 hour to 72 hours, preferably from 1 hour to 48 hours. Rhodium complexes are immobilized on this support or on neutralized support by sodium hydroxide. The reaction is carried out in water/ethanol mixture (1/1 volume ratio) at 20° C. for 1–24 hours.

Suitable rhodium compounds include chlorobis(ethylene) rhodium dimer $[RhCl(C_2H_4)_2]_2$, chlorocarbonylbis (triphenylphosphine) rhodium $RhCl(CO)(PPh_3)_2$, rhodium dicarbonyl chloride $[RhCl(CO)_2]_2$, chlorotris(triphenylphosphine) rhodium $RhCl(PPh_3)_3$, hexarhodium hexadecacarbonyl $Rh_6(CO)_{16}$, hydridocarbonyltris(triphenylphosphine) rhodium $RhH(CO)(PPh_3)_3$, rhodium tribromide dihydrate $RhBr_3.2H_2O$, rhodium chloride $RhCl_3$, rhodium trichloride hydrate $RhCl_3.xH_2O$, rhodium iodide $RhI_3$, rhodium oxide hydrate $Rh_2O_3.5H_2O$, tetrarhodium dodecacarbonyl $Rh_4.(CO)_{12}$ and the corresponding rhodium compounds. Rhodium trichloride trihydrate and rhodium carbonyl compounds are particularly preferred.

These polystyrene immobilized rhodium catalyst described above can be used for the hydroformylation of olefins whose molecule contains from 2 to 20, preferably 2 to 8 carbon atoms, such as ethylene, propylene, 1-butene, 1-pentene, 1-hexene, 2-hexene, 1-heptene and 1-octene in the aqueous phase or in an organic medium. They are particularly valuable in the hydroformylation of ethylene, propylene, butene-1, hexene-1 and styrene. The reaction is preferred carried out at temperatures of from 10° to 180° C., especially from 20° to 150° C., at the pressures of from 1 to 70 atm, especially from 1 to 50 atm. The hydroformylation process according to the invention can be carried out continuously or discontinuously.

Especially, tertiary phosphine is used to improve the selectivity to n-butanal. Triphenylphosphine is added from 0.01 to 10 wt. % to rhodium.

The above described polystyrene immobilized rhodium catalyst has several advantages and illustrated following.

The hydroformylation of olefins is usually carried out in an organic medium. However, the catalyst in this invention offers a high yield in an aqueous phase as well as in an organic medium. The aqueous phase reaction offers an easy separation of products, solvent and catalyst and reduce the pollution problem.

The catalyst can be reused because of the immobilization on the polymer support and continuous reaction is possible.

The reaction can be carried out in the milder condition and the catalyst can be reused easily. These advantages reduce the production cost.

The following examples illustrate the invention and are not intended to limit the invention, but rather, are presented for purpose of illustration.

EXAMPLE 1

The dried polymer beads prepared as set forth in following method.

$RhCl_3$ $3H_2O$, distilled water and ethanol were charged to a flask and heated at 60° to 100° C. for 6 hours under stirring. The mixture was then cooled to about 20° C. The solid product was then filtered and washing was continued to remove all soluble materials. The final product was then dried under vacuum at 60° to 80° C. for 2 days and the product had a rhodium content of 0.4 to 11.8 wt %.

Preparation of the polymer support:

A mixture of 2% crosslinked poly(styrene-divinylbenzene) copolymer beads (25.0 g), chloromethyl methylether (150 cm$^3$, CAUTION: CANCER SUSPECT AGENT) and 7.1 g of tin tetrachloride was introduced into a 250 cm$^3$ Erlenmeyer flask equipped with a central stirrer system, a thermometer and a reflux condenser. The chloromethylation was carried out at room temperature under stirring for 3 hours. The resultant beads were then filtered and washed with methanol and dioxane solution (containing 10% hydrochloric acid). After washing the resultant polymer beads with pure dioxane, unreacted chlorine in the beads was removed with tetrahydrofuran by extraction method and the beads were dried under high vacuum for 24 hours at 70° to 90° C. The chlorine content of polymer beads is 17.5 wt %.

A mixture of chlorodiphenylphosphine (12 cm$^3$) and lithium (2.1 g) was charged to a tetrahydrofuran solution (150 cm$^3$) under nitrogen atmosphere with stirring at room temperature for 24 hours. The mixture was then transferred to a 250 cm$^3$ Erlenmeyer flask containing the chloromethylated polymer beads by syringe and stirred for 24 hours. The resulting polymer beads were filtered and washed with 10% NH$_4$Cl aqueous solution, methanol and benzene and dried under vacuum for 24 hours. The phosphine content of resulting polymer beads is 8 wt. %.

Phosphinated poly(styrene-divinylbenzene) copolymer beads (5 g) obtained by the above procedures and 1,2-dichloroethane (20 cm$^3$) were mixed at 60° to 100° C. for 6 to 18 hours and sulfuric acid (99 percent, 50 cm$^3$) was added slowly to this mixture and stirred at 80° to 120° C. for 2 days. The resulting polymer was then filtered and washed with distilled water and acetone, repeatedly and dried under vacuum for 2 days. The sulfur content of resulting polymer beads is 5 wt %.

EXAMPLE 2

The dried polymer support prepared as set forth in Example 1 was treated with sodium hydroxide solution and mixed with $RhCl(CO)(PPh_3)_2$ in benzene and the mixture was reacted at about 60° C. for 5 days under stirring. The final product was filtered and washed with benzene to remove all soluble materials. The final product was then dried under vacuum at 60° to 80° C. for 2 days and the product had a rhodium content of about 4 wt %.

EXAMPLE 3

Hydroformylation of propylene was conducted at a constant temperature and pressure in a 1000 cm³ autoclave (Parr, model #4521). A constant reaction pressure was maintained by introducing $H_2/CO$ gas mixture from a gas reservoir via a forward pressure regulator preset at a reaction pressure. The catalyst solution was transferred to the reactor. The catalyst prepared by the procedure in Example 1 0.1 g, representing 0.0037 gram atom of Rh, and 300 cm³ of distilled water were introduced into a stainless steel autoclave. The reactor was purged for 30 minutes with nitrogen, 4.6 g (0.109 mol) of propylene were then introduced and a pressure was established with a mixture of $CO+H_2$. The molar ratio of $CO/H_2$ was varied. The autoclave was then heated to 100° C. and agitated for 4 hours at this temperature. The reaction rate and selectivity to n-butanal were calculated from the product analysis with gas chromatography (Tracor 560). The rate and selectivity dependence with respect to the hydrogen and carbon monoxide pressure ratio at 100° C. has been described in Table 1.

TABLE 1

The effect of hydrogen and carbon monoxide pressure on the activity and selectivity in the hydroformylation of propylene. (Rh concentration = 0.12 mmol/liter)

| $H_2$ (atm) | CO (atm) | Reaction rate (mol/g Rh · min × $10^4$) | Selectivity (n/i) |
|---|---|---|---|
| 5 | 5 | 1.9 | 1.4 |
| 10 | 5 | 6.1 | 1.6 |
| 20 | 5 | 8.4 | 1.7 |
| 30 | 5 | 10.3 | 1.8 |
| 40 | 5 | 11.4 | 1.9 |
| 5 | 10 | 4.4 | 1.6 |
| 5 | 15 | 3.8 | 1.6 |
| 5 | 20 | 3.6 | 1.6 |
| 5 | 30 | 3.6 | 1.5 |
| 10 | 10 | 3.4 | 1.5 |
| 15 | 15 | 7.4 | 2.0 |
| 20 | 20 | 6.5 | 1.8 |

EXAMPLE 4

The catalyst prepared by the procedure in Example 1 0.1 g, representing 0.0118 gram atom of Rh and 180 cm³ of distilled water were introduced into a stainless steel autoclave equipped with an agitation system. The reactor was purged for 30 minutes with nitrogen, 12.6 g (0.300 mol) of propylene were then introduced and a pressure was established with an equimolar mixture of $CO+H_2$ (total pressure: 30 atm). The autoclave was then heated to 100° C. and agitated for 4 hours at this temperature. In order to improve the selectivity to n-butanal, triphenylphosphine is introduced to the reaction mixture about 0.02–0.2 g. The effect of triphenylphosphie on the activity and selectivity in the hydroformylation of propylene has been described in Table 2.

TABLE 2

The effect of excess triphenylphosphine on the activity and selectivity in the hydroformylation of propylene. (Rh concentration = 0.12 mmol/liter)

| Excess $PPh_3$ (gr) | Reaction rate (mol/g Rh-min × $10^4$) | Selectivity (n/i) |
|---|---|---|
| 0.00 | 20.0 | 1.2 |
| 0.02 | 9.2 | 2.8 |
| 0.05 | 11.3 | 3.1 |
| 0.10 | 8.8 | 2.9 |
| 0.20 | 8.7 | 3.3 |

EXAMPLE 5

Example 3 was repeated with recycling the catalysts prepared in Example 1 and Example 2. The catalyst prepared by the procedure in Example 1 and Example 2 and 180 cm³ of distilled water were introduced into a stainless steel autoclave equipped with an agitation system. The reactor was purged for 30 minutes with nitrogen, 12.6 g (0.300 mol) of propylene were then introduced and a pressure was established with an equimolar mixture of $CO+H_2$ (total pressure: 30 atm). The autoclave was then heated to 100° C. and agitated for 4 hours at this temperature. The activity of the reused catalyst has been described in Table 3.

TABLE 3

The activity of the catalyst in the hydroformylation of propylene. (Rh concentration = 0.12 mmol/liter) Rate: mol/g Rh.min × $10^4$.

| catalyst | recycle | | | | | |
| | 1 | 2 | 3 | 4 | 5 | 6 |
|---|---|---|---|---|---|---|
| catalyst in Example 1 (Rh: 11.8 wt. %) | 2.0 | 1.9 | 1.6 | 1.3 | 1.3 | 1.1 |
| catalyst in Example 2 (Rh: 1.6 wt. %) | 3.3 | 3.3 | 3.4 | 3.4 | 3.9 | 4.6 |

EXAMPLE 6

The catalyst containing a different amount of rhodium prepared by the procedure in Example 1 and 300 cm³ of distilled water were introduced into a 1000 cm³ stainless steel autoclave equipped with an agitation system. The reactor was purged for 30 minutes with nitrogen, 4.6 g (0.109 mol) of propylene were then introduced and a pressure was established with an equimolar mixture of $CO+H_2$ (total pressure: 30 atm). The autoclave was then heated to 100° C. and agitated for 4 hours at this temperature. The effect of rhodium loading on the activity and selectivity of the catalyst in the hydroformylation of propylene has been described in Table 4.

TABLE 4

The effect of rhodium loading on the activity and selectivity in the hydroformylation of propylene. (Rh concentration = 0.12 mmol/liter)

| Rhodium loading (wt. %) | Reaction rate (mol/g Rh · min × $10^4$) | Selectivity (n/i) |
|---|---|---|
| 0.4 | 14.1 | 1.7 |
| 0.8 | 19.3 | 1.7 |
| 1.5 | 15.9 | 1.6 |
| 3.4 | 30.0 | 1.2 |
| 3.7 | 7.4 | 2.0 |

EXAMPLE 7

The soluble catalyst, RhCl₃ 3H₂O, and insoluble catalyst, RhCl(CO)(PPh₃)₃, in the aqueous medium were used for the hydroformylation of propylene in the aqueous phase in order to compare the activity of a polymer immobilized catalyst. The activity and selectivity of these catalysts have been described in Table 5.

TABLE 5

The activity and selectivity of the homogeneous rhodium catalyst in the hydroformylation of propylene in aqueous reaction.

| Catalyst | Reaction rate (mol/g Rh · min × 10⁴) | Selectivity (n/i) |
|---|---|---|
| RhCl₃3H₂O | 3.2 | 1.1 |
| RhCl(CO)(PPh₃)₂ | 3.1 | 1.7 |

Although the invention has been described in considerable detail with particular reference to certain preferred embodiments thereof, variations and modifications can be effected within the spirit and scope of the invention as described hereinbefore, and as defined in the appended claims.

What is claimed is:

1. A process for preparation of a solid, particulate, catalytic complex for the hydroformylation of olefins, comprising the steps: (a) sulfonating a phosphinated polystyrene containing from 0.1 to 10 wt. % of phosphine to a solid product containing about from 0.1 to 10 wt. % of sulfur; and (b) immobilizing rhodium complexes on the resultant sulfonated solid.

2. A process according to claim 1, wherein said rhodium complex is immobilized at a weight percent in the range of about from 0.1 to 15 wt. %.

3. A process according to claim 1, wherein said phosphinated polystyrene is sulfonated by a concentrated sulfuric acid in the temperature range of about from 15° to 130° C., for about from one to 72 hours.

4. A process according to claim 1, wherein said rhodium complex is selected from the group consisting of the following compounds: Chlorobis(ethylene) rhodium dimer [RhCl(C₂H₄)₂]₂, chlorocarbonylbis(triphenylphosphine) rhodium RhCl(CO) (PPh₃)₂, rodium dicarbonyl chloride [RhCl(CO)₂]₂, chlorotris (triphenylphosphine) rhodium RhCl(PPh₃)₃, hexarhodium hexadecacarbonyl Rh₆(CO)₁₆, hydridocarbonyl-tris (triphenylphosphine) rhodium RhH(CO) (PPh₃)₃, rhodium tribromide dihydrate RhBr₃.2H₂O, rhodium chloride RhCl₃, rhodium trichloride hydrate RhCl₃.xH₂O, rhodium iodide RhI₃, rhodium oxide hydrate Rh₂O₃.5H₂O, and tetrarhodium dodecacarbonyl Rh₄(CO)₁₂.

5. A process according to claim 4, further comprising the steps of neutralizing the sulfonated polystyrene containing from 0.1 to 10 wt. % of sulfur and immobilizing rhodium complexes on the resultant sulfonated solid.

6. A process according to claim 5, wherein the amount of rhodium in the catalyst is about from 0.1 to 15 wt. % of rhodium.

7. A solid, particulate, catalytic complex for the hydroformylation of olefins prepared by a process according to any one of claims 1 to 6.

* * * * *